(12) United States Patent
Martin et al.

(10) Patent No.: US 8,954,074 B2
(45) Date of Patent: Feb. 10, 2015

(54) METHOD AND APPARATUS FOR TRIGGERING CELL RESELECTION BASED ON A RESOURCE SUSPENSION

(75) Inventors: Brian Martin, Surrey (GB); Keiichi Kubota, Surrey (GB); Tao Chen, Salo (FI)

(73) Assignee: Broadcom Corporation, Irvine, CA (US)

( * ) Notice: Subject to any disclaimer, the term of this patent is extended or adjusted under 35 U.S.C. 154(b) by 147 days.

(21) Appl. No.: 13/210,201

(22) Filed: Aug. 15, 2011

(65) Prior Publication Data

US 2013/0045741 A1  Feb. 21, 2013

(51) Int. Cl.
*H04W 36/20* (2009.01)

(52) U.S. Cl.
CPC .................................... *H04W 36/20* (2013.01)
USPC ........... 455/436; 455/437; 455/438; 455/439; 455/435.1; 455/435.2; 370/278; 370/332; 370/250; 370/328; 370/331

(58) Field of Classification Search
USPC ................ 455/436–439, 436.3, 435.1–435.3; 370/278, 331–332, 250, 328
See application file for complete search history.

(56) References Cited

U.S. PATENT DOCUMENTS

| | | | |
|---|---|---|---|
| 8,285,285 B2 * | 10/2012 | Kitazoe et al. | 455/436 |
| 2008/0267061 A1 | 10/2008 | DiGirolamo et al. | |
| 2009/0168728 A1 | 7/2009 | Pani et al. | |
| 2009/0247161 A1 * | 10/2009 | Pani et al. | 455/435.3 |
| 2012/0243423 A1 * | 9/2012 | Englund et al. | 370/250 |

FOREIGN PATENT DOCUMENTS

| | | |
|---|---|---|
| WO | WO 2006/106561 A1 | 10/2006 |
| WO | WO 2009/055804 A2 | 4/2009 |
| WO | WO 2009/088868 A2 | 7/2009 |
| WO | WO 2009/099368 A2 | 8/2009 |
| WO | WO-2009/117667 | 9/2009 |
| WO | WO 2009/123544 A1 | 10/2009 |

OTHER PUBLICATIONS

Search and Examination Report from United Kingdom Application No. GB1114029.0, dated Dec. 8, 2011.
3GPP TSG-RAN WG3 #59-bis Mar. 31-Apr. 3, 2008, Shenzen, China; R3-080732; Qualcomm.
3GPP TSG RAN WG1 Meeting #51bis Jan. 14-18, 2008, Sevilla, Spain; R1-080219; Huawei.

(Continued)

*Primary Examiner* — Kiet Doan
*Assistant Examiner* — Michael T Vu
(74) *Attorney, Agent, or Firm* — Stanton IP Law

(57) ABSTRACT

A method, apparatus and computer program product are provided in order to trigger a reselection of a serving cell in an instance in which a mobile terminal may be creating neighbor cell interference. Based upon received reselection data, the mobile terminal may release and/or suspend a network resource, such as an enhanced dedicated channel in order to trigger a reselection of a new serving cell. In this regard, a method is provided that includes determining the presence of a reselection condition based on reselection data. In an instance in which the presence of the reselection condition is determined, the method includes causing a network resource to be modified. The method also includes causing a reselection of a serving cell.

15 Claims, 4 Drawing Sheets

(56) References Cited

OTHER PUBLICATIONS

"Discussion on the need for UL interference control mechanisms in CELL_FACH state;" InterDigital; 3GPP TSG-RAN WG2 Meeting #74; dated May 9-13, 2011.

International Search Report for Application No. PCT/IB2012/054153; dated Dec. 19, 2012.

"On the benefits of signaling based interference control in CEL_FACH;" Qualcomm Incorporated; 3GPP TSG-RAN WG2 Meeting #74; dated May 9-13, 2011.

* cited by examiner

METHOD AND APPARATUS FOR TRIGGERING CELL RESELECTION BASED ON A RESOURCE SUSPENSION

TECHNOLOGICAL FIELD

Embodiments of the present invention relate generally to communications technology and, more particularly, to suspension and/or release of a resource for triggering reselection of a serving cell.

BACKGROUND

The communications between a mobile terminal and a serving cell, such as the uplink communications from the mobile terminal to the serving cell, may sometimes create interference with neighbor cells. This interference may inhibit the operation of the neighbor cells or may at least cause the mobile terminal and/or the neighbor cells to operate less efficiently. In some operational states, such as a CELL_DCH state, the mobile terminal and the serving cell may monitor the neighbor cells in such a manner that instances of neighbor cell interference may be identified and the operation of the mobile terminal and/or the serving cell may be modified in such a manner as to reduce the potential for the neighbor cell interference. Indeed, in the CELL_DCH state, the neighbor cells may be added to the active set so as to be involved in uplink power control. In this regard, the mobile terminal may receive signals from the serving cell as well as the neighbor cells. As such, neighbor cells may identify instances in which the mobile terminal is creating interference such that the mobile terminal may reduce its uplink power in an effort to correspondingly reduce the neighbor cell interference. More particularly, for a mobile terminal operating in a CELL_DCH state, the uplink power from the mobile terminal may be controlled via relative grants from neighbor cells within the active set of the mobile terminal.

In other operational states, however, the mobile terminal may not communicate with the neighbor cells in the same manner and, as such, may not be able to identify instances of potential neighbor cell interference. For example, a mobile terminal in a CELL_FACH state may only receive signals from the serving cell. As such, in instances in which the mobile terminal is creating interference for the neighbor cells, the neighbor cells are unable to communicate with the mobile terminal in order to request that the power, such as the uplink power, be reduced in an effort to correspondingly reduce the neighbor cell interference. For example, in contrast to the relative grants from neighbor cells to a mobile terminal in a CELL_DCH state that serve to control the uplink power, a mobile terminal operating in the CELL_FACH state may not have similar control of its uplink power since the uplink power of the mobile terminal may only be controlled by the serving cell using absolute grants without consideration of possible neighbor cell interference. As such, a mobile terminal that is creating neighbor cell interference may impair the operation of the neighbor cells and, in some instances, may suffer from radio link failure.

In Release 8 of the Third Generation Partnership Project (3GPP) specification, an enhanced uplink for a mobile terminal in the CELL_FACH state in the idle mode was introduced. This enhanced uplink is termed a common enhanced dedicated channel (Common E-DCH). As such, mobile terminals may utilize the E-DCH in other radio resource control (RRC) states in addition to or other than the CELL_DCH state. Notwithstanding the potential for the creation of neighbor cell interference to be created by the uplink transmissions of a mobile terminal in the CELL_FACH state, it is anticipated that mobile terminals will frequently operate in the CELL_FACH state, such as to perform infrequent or bursty data transmissions, and that operation of mobile terminals in the CELL_FACH state may increase as a result of the introduction of the E-DCH. As such, the issues relating to potential neighbor cell interference while a mobile terminal is operating in the CELL_FACH state may also become more frequent and problematic.

A number of signaling based methods have been proposed in an effort to provide some measure of interference control for the neighbor cells in instances in which a mobile terminal is operating in the CELL_FACH state. However the proposals have generally suffered from various drawbacks including, for example, increased complexity for the mobile terminal and/or the serving cell or the failure to address all use cases or scenarios.

BRIEF SUMMARY

A method, apparatus and computer program product are therefore provided according to an example embodiment in order to trigger a reselection of a serving cell in an instance in which a mobile terminal may be creating interference with a neighbor cell. Based upon received reselection data, the mobile terminal may release and/or suspend a network resource, such as an enhanced dedicated channel (E-DCH), in order to trigger a reselection of a new serving cell. In one embodiment, the method, apparatus and computer program product may trigger reselection of a new cell in an instance in which neighbor cell interference has been potentially created while the mobile terminal is in the CELL_FACH state. As such, the method, apparatus and computer program product of example embodiments of the present invention may reduce neighbor cell interference, thereby improving overall system performance.

In one embodiment, a method is provided that includes determining the presence of a reselection condition based on reselection data. In an instance in which the presence of the reselection condition is determined, the method includes causing a network resource to be modified. The method also includes causing a reselection of a serving cell.

In another embodiment, an apparatus is provided that includes at least one processor and at least one memory including computer program code with the at least one memory and the computer program code configured to, with the at least one processor, cause the apparatus at least to determine the presence of a reselection condition based on reselection data. The at least one memory and the computer program code are also configured to, with the at least one processor, cause the apparatus at least to cause a network resource to be modified in an instance in which the presence of the reselection condition is determined. The at least one memory and the computer program code are also configured to, with the at least one processor, cause the apparatus at least to cause a reselection of a serving cell.

In a further embodiment, a computer program product is provided that includes at least one non-transitory computer-readable storage medium having computer-readable program instructions stored therein, the computer-readable program instructions including program instructions are configured to determine the presence of a reselection condition based on reselection data. The computer-readable program instructions of this embodiment also include program instructions configured to cause a network resource to be modified in an instance in which the presence of the reselection condition is determined. The computer-readable program instructions of this embodiment also include program instructions configured to cause a reselection of a serving cell.

In yet another embodiment, an apparatus is provided that includes means for determining the presence of a reselection condition based on reselection data. The apparatus of this embodiment also includes, in an instance in which the presence of the reselection condition is determined, means for causing a network resource to be modified. The apparatus of this embodiment also includes means for causing a reselection of a serving cell.

In one embodiment, a method is provided that includes determining the presence of uplink interference while a mobile terminal is in a CELL_FACH state. The method of this embodiment also causes an E-DCH to be modified in an instance in which the presence of uplink interference is determined. The method of this embodiment also includes causing a reselection of a serving cell.

In another embodiment, an apparatus is provided that includes at least one processor and at least one memory including computer program code with the at least one memory and the computer program code configured to, the at least one processor, cause the apparatus at least to determine the presence of uplink interference while a mobile terminal is in a CELL_FACH state. The at least one memory and the computer program code are also configured to, with the at least one processor, cause the apparatus of this embodiment to cause an E-DCH to be modified in an instance in which the presence of uplink interference is determined. The at least one memory and the computer program code are also configured to, with the at least one processor, cause the apparatus of this embodiment to cause a reselection of a serving cell.

In a further embodiment, a computer program product is provided that includes at least one non-transitory computer-readable storage medium having computer-readable program instructions stored therein, the computer-readable program instructions including program instructions configured to determine the presence of uplink interference while a mobile terminal is in a CELL_FACH state. The computer-readable program instructions of this embodiment also include program instructions configured to cause the apparatus of this embodiment to cause an E-DCH to be modified in an instance in which the presence of uplink interference is determined. The computer-readable program instructions of this embodiment also include program instructions configured to cause a reselection of a serving cell.

In yet another embodiment, an apparatus is provided that includes means for determining the presence of uplink interference while a mobile terminal is in a CELL_FACH state. The apparatus of this embodiment also includes means for causing an E-DCH to be modified in an instance in which the presence of uplink interference is determined. The apparatus of this embodiment also includes means for causing a reselection of a serving cell.

BRIEF DESCRIPTION OF THE DRAWINGS

Figure 1:
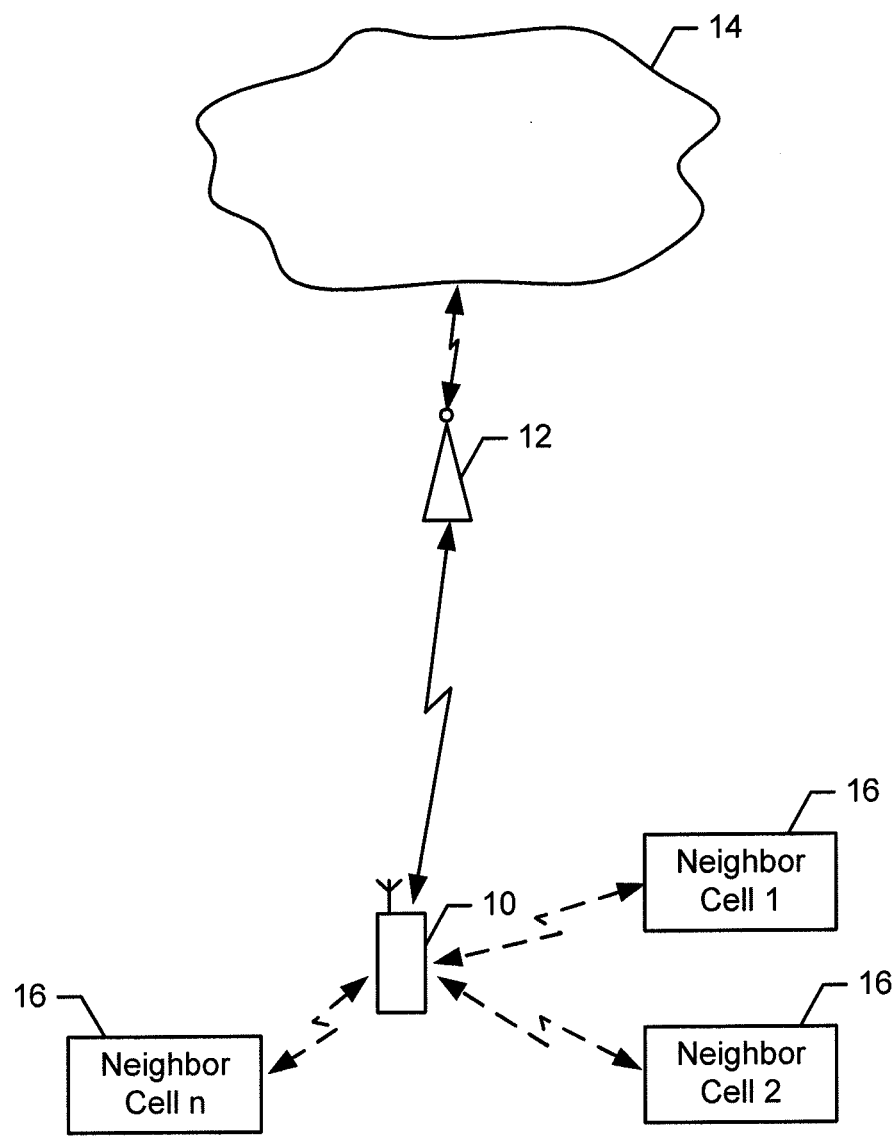
Figure 2:
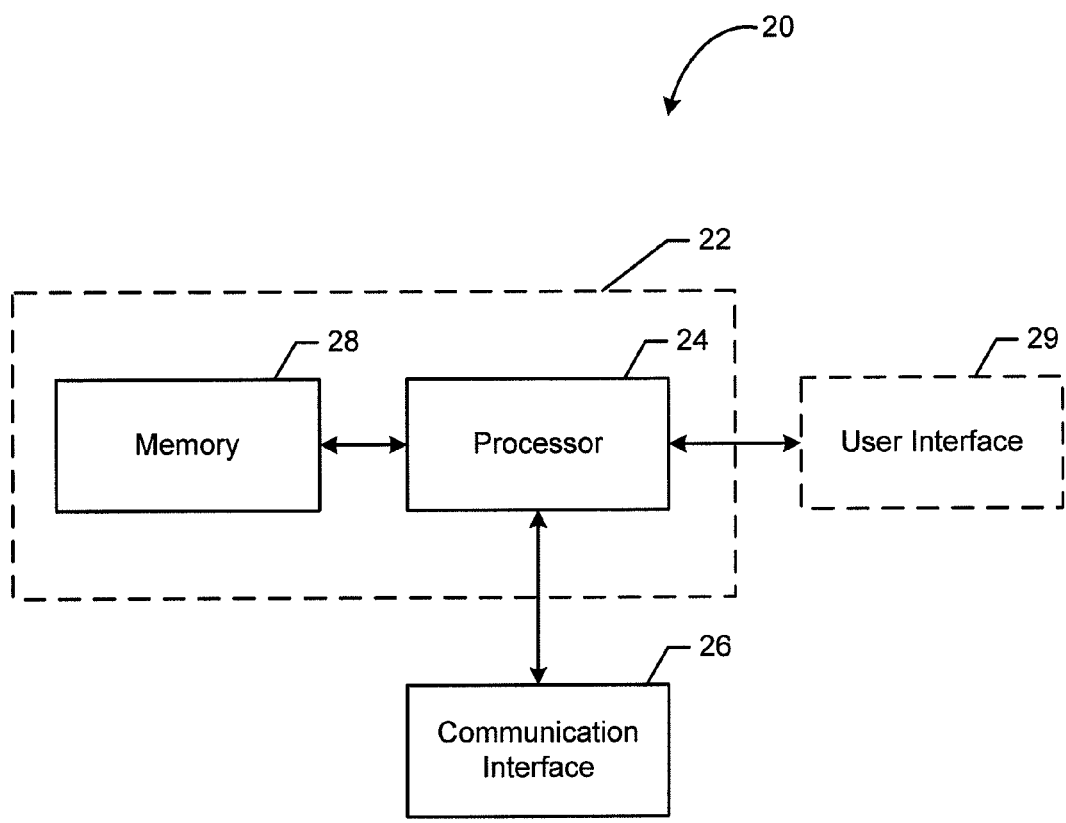
Figure 3:
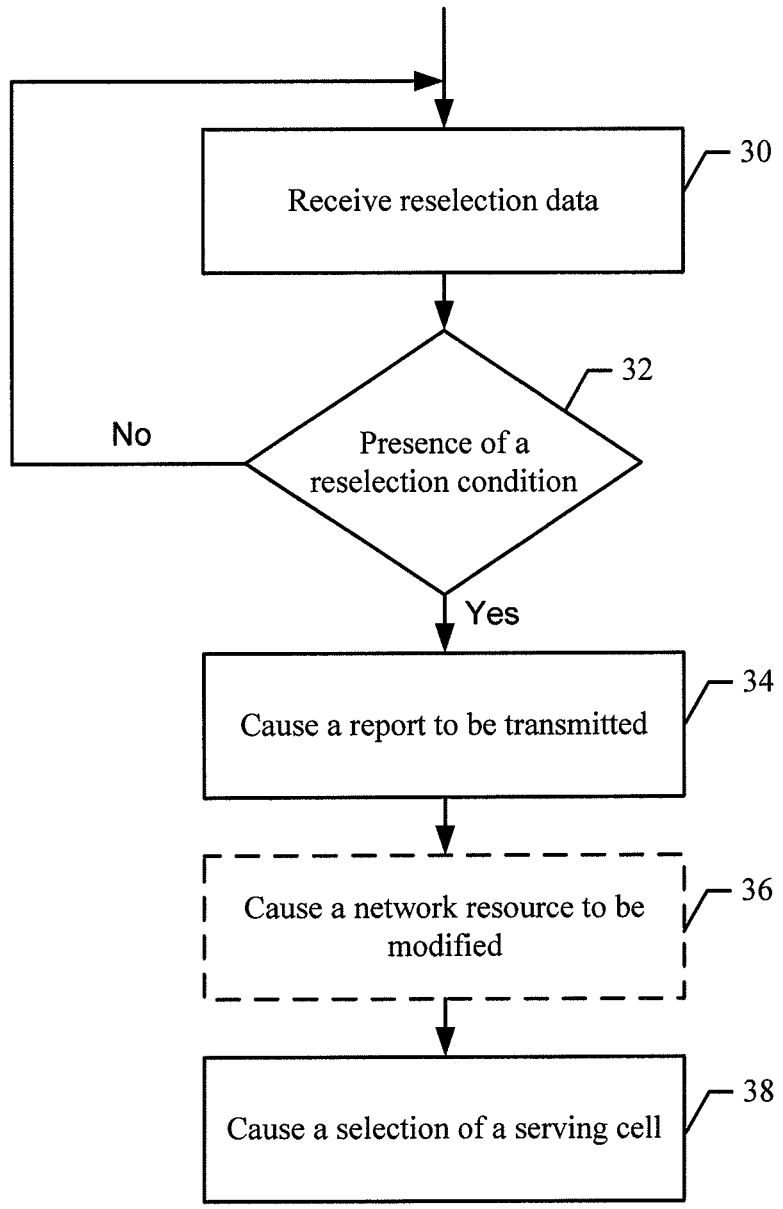
Figure 4:
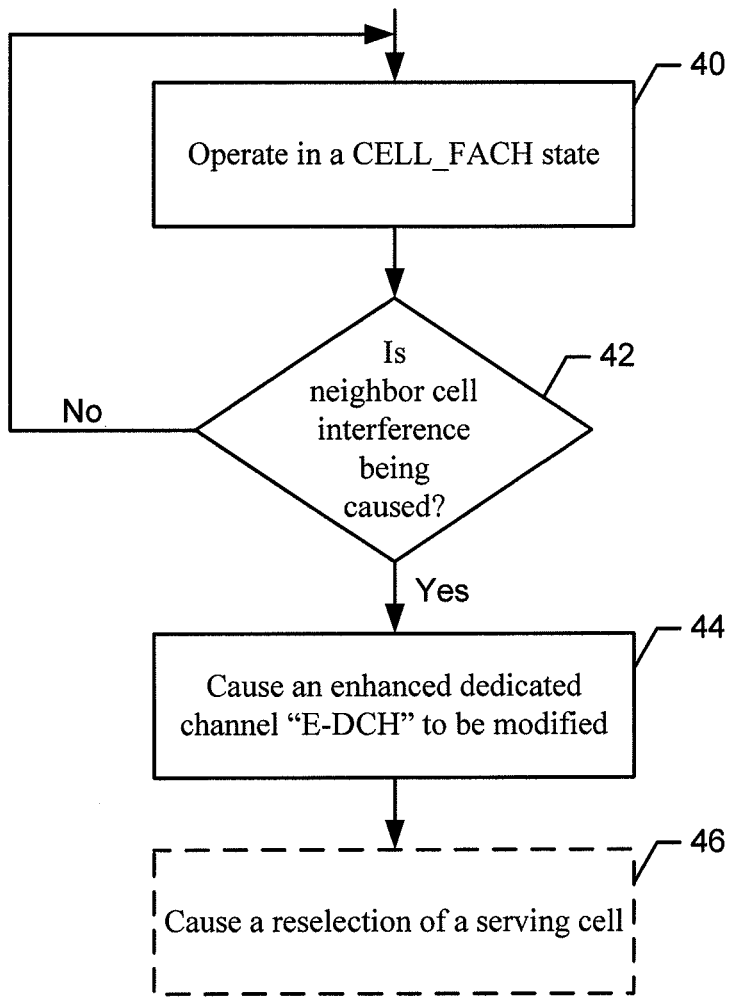

Having thus described the example embodiments of the invention in general terms, reference will now be made to the accompanying drawings, which are not necessarily drawn to scale, and wherein:

FIG. 1 is a schematic representation of a system having a serving cell and one or more neighbor cells that may experience interference created by the mobile terminal and that may benefit from an embodiment of the present invention;

FIG. 2 is a block diagram of an apparatus that may be embodied by a mobile terminal in accordance with one embodiment of the present invention;

FIG. 3 is a flow chart illustrating operations performed in accordance with one embodiment of the present invention; and FIG. 4 illustrates the flow chart of operations performed in accordance with another embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

As used in this application, the term 'circuitry' refers to all of the following: (a) hardware-only circuit implementations (such as implementations in only analog and/or digital circuitry) and (b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and (c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or application specific integrated circuit for a mobile phone or a similar integrated circuit in server, a cellular network device, or other network device.

A method, apparatus and computer program product of an example embodiment of the present invention are configured to determine instances in which a mobile terminal may be creating neighbor cell interference, such as a result of interference created by uplink transmissions from the mobile terminal to a serving cell. In accordance with an example embodiment, a network resource, such as an E-DCH, may be modified (e.g., suspended and/or released) by the mobile terminal that may be creating neighbor cell interference. Based upon the modified network resource, the mobile terminal may select a new serving cell in an effort to reduce neighbor cell interference. In one embodiment, the mobile terminal identifies the potential for neighbor cell interference while in the CELL_FACH state, thereby permitting neighbor cell interference to be reduced or otherwise addressed even while the mobile terminal is in the CELL_FACH state.

Although the method, apparatus and computer program product may be implemented in a variety of different systems, one example of such a system is shown in FIG. 1, which includes a first communication device (e.g., mobile terminal 10) that is capable of communication via a serving cell 12, such as a base station, a Node B, an evolved Node B (eNB) or other access point, with a network 14 (e.g., a core network). While the network may be configured in accordance with Long Term Evolution (LTE) or LTE-Advanced (LTE-A), other networks may support the method, apparatus and computer program product of embodiments of the present invention including those configured in accordance with wideband code division multiple access (W-CDMA), CDMA2000, global system for mobile communications (GSM), general packet radio service (GPRS) and/or the like.

The network 14 may include a collection of various different nodes, devices or functions that may be in communication with each other via corresponding wired and/or wireless interfaces. For example, the network may include one or more cells, including serving cell 12 and one or more neighbor cells 16 (designated neighbor cell 1, neighbor cell 2, . . . neighbor cell n in the embodiment of FIG. 1), each of which may serve a respective coverage area. The serving cell and the neighbor cells could be, for example, part of one or more cellular or mobile networks or public land mobile networks (PLMNs). In turn, other devices such as processing devices (e.g., personal computers, server computers or the like) may be coupled to the mobile terminal 10 and/or other communication devices via the network.

A communication device, such as the mobile terminal 10 (also known as user equipment (UE)), may be in communication with other communication devices or other devices via the serving cell 12 and, in turn, the network 14. In some cases, the communication device may include an antenna for transmitting signals to and for receiving signals from a serving cell.

In some example embodiments, the mobile terminal 10 may be a mobile communication device such as, for example, a mobile telephone, portable digital assistant (PDA), pager, laptop computer, or any of numerous other hand held or portable communication devices, computation devices, content generation devices, content consumption devices, or combinations thereof. As such, the mobile terminal 10 may include one or more processors that may define processing circuitry either alone or in combination with one or more memories. The processing circuitry may utilize instructions stored in the memory to cause the mobile terminal 10 to operate in a particular way or execute specific functionality when the instructions are executed by the one or more processors. The mobile terminal 10 may also include communication circuitry and corresponding hardware/software to enable communication with other devices and/or the network 14.

In one embodiment, for example, the mobile terminal 10 and/or the serving cell 12 may be embodied as or otherwise include an apparatus 20 as generically represented by the block diagram of FIG. 2. While the apparatus 20 may be employed, for example, by a mobile terminal 10 or a serving cell 12, it should be noted that the components, devices or elements described below may not be mandatory and thus some may be omitted in certain embodiments. Additionally, some embodiments may include further or different components, devices or elements beyond those shown and described herein.

As shown in FIG. 2, the apparatus 20 may include or otherwise be in communication with processing circuitry 22 that is configurable to perform actions in accordance with example embodiments described herein. The processing circuitry may be configured to perform data processing, application execution and/or other processing and management services according to an example embodiment of the present invention. In some embodiments, the apparatus or the processing circuitry may be embodied as a chip or chip set. In other words, the apparatus or the processing circuitry may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The apparatus or the processing circuitry may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 22 may include a processor 24 and memory 28 that may be in communication with or otherwise control a communication interface 26 and, in some cases, a user interface 30. As such, the processing circuitry may be embodied as a circuit chip (e.g., an integrated circuit chip) configured (e.g., with hardware, software or a combination of hardware and software) to perform operations described herein. However, in some embodiments taken in the context of the mobile terminal 10, the processing circuitry may be embodied as a portion of a mobile computing device or other mobile terminal.

The user interface 30 (if implemented) may be in communication with the processing circuitry 22 to receive an indication of a user input at the user interface and/or to provide an audible, visual, mechanical or other output to the user. As such, the user interface may include, for example, a keyboard, a mouse, a joystick, a display, a touch screen, a microphone, a speaker, and/or other input/output mechanisms. The apparatus 20 need not always include a user interface. For example, in instances in which the apparatus is embodied as a serving cell 12, the apparatus may not include a user interface. As such, the user interface is shown in dashed lines in FIG. 2.

The communication interface 26 may include one or more interface mechanisms for enabling communication with other devices and/or networks. In some cases, the communication interface may be any means such as a device or circuitry embodied in either hardware, or a combination of hardware and software that is configured to receive and/or transmit data from/to a network 14 and/or any other device or module in communication with the processing circuitry 22, such as between the mobile terminal 10 and the serving cell 12. In this regard, the communication interface may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods.

In an example embodiment, the memory 28 may include one or more non-transitory memory devices such as, for example, volatile and/or non-volatile memory that may be either fixed or removable. The memory may be configured to store information, data, applications, instructions or the like for enabling the apparatus 20 to carry out various functions in accordance with example embodiments of the present invention. For example, the memory could be configured to buffer input data for processing by the processor 24. Additionally or alternatively, the memory could be configured to store instructions for execution by the processor. As yet another alternative, the memory may include one of a plurality of databases that may store a variety of files, contents or data sets. Among the contents of the memory, applications may be stored for execution by the processor in order to carry out the functionality associated with each respective application. In some cases, the memory may be in communication with the processor via a bus for passing information among components of the apparatus.

The processor 24 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor may be configured to execute instructions stored in the memory 28 or otherwise accessible to the processor. As such, whether configured by hardware or by a combination of hardware and software, the processor may represent an entity (e.g., physically embodied in circuitry—in the form of processing circuitry 22) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the operations described herein.

Referring now to FIGS. 3 and 4, flowcharts illustrating the operations performed by a method, apparatus and computer program product, such as apparatus 20 of FIG. 2, from the perspective of a mobile terminal 10 in accordance with one embodiment of the present invention are illustrated. It will be understood that each block of the flowcharts, and combinations of blocks in the flowcharts, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device 28 of an apparatus employing an embodiment of the present invention and executed by a processor 24 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 3 and 4, when executed, convert a computer or processing circuitry into a particular machine configured to perform an example embodiment of the present invention. Accordingly, the operations of each of FIGS. 3 and 4 define an algorithm for configuring a computer or processing circuitry 22, e.g., processor, to perform an example embodiment. In some cases, a general purpose computer may be provided with an instance of the processor which performs the algorithm of a respective one of FIGS. 3 and 4 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowchart, and combinations of blocks in the flowcharts, can be implemented by special purpose hardware-based computer systems which perform the specified functions, or combinations of special purpose hardware and computer instructions.

In some embodiments, certain ones of the operations above may be modified or further amplified as described below. Moreover, in some embodiments additional optional operations may also be included (some examples of which are shown in dashed lines in FIGS. 3 and 4). It should be appreciated that each of the modifications, optional additions or amplifications below may be included with the operations above either alone or in combination with any others among the features described herein.

FIG. 3 is a flow chart illustrating serving cell reselection performed in accordance with one embodiment of the present invention. Referring now to FIG. 3, as shown in operation 30, the apparatus 20 embodied, for example, by a mobile terminal 10, may include means, such as the processing circuitry 22, the processor 24, the communications interface 26 or the like, for receiving reselection data. In an embodiment, reselection data may interference data, reselection criteria, and/or a network command. Reselection criteria, in one embodiment, is that criteria that would generally cause an apparatus 20, such as mobile terminal 10, to transition from a current serving cell, such as serving cell 12, to another serving cell, such as neighbor cell 16 when a neighbor cell 16 received power is determined to be higher than the serving cell 12 received power. In an example embodiment, and as described above, the received reselection data may also include interference data. Interference data may indicate the level of interference between a mobile terminal, such as mobile terminal 10, and one or more neighbor cells, such as neighbor cell 16.

As shown in decision operation 32 of FIG. 3, the apparatus 20 may also include means, such as the processing circuitry 22, the processor 24 or the like, for determining the presence of a reselection condition. In an example embodiment, a reselection condition may occur in an instance in which it is determined, such as by the processor, that the reselection criteria have been met, in an instance in which it is determined, again such as by the processor, that interference exists between the mobile terminal and one or more neighboring cells and/or in an instance in which a network command is received, such as by the communications interface, that indicates that the mobile terminal, for example, is to release a network resource, such as the E-DCH. Potential interference between the mobile terminal 10 and neighbor cells 16 may be identified in various manners including, for example, by analyzing the transmission power of the mobile terminal, path loss and/or neighbor cells uplink interference levels may be analyzed.

In one embodiment, the apparatus 20, such as the processor 24, may determine the transmission power of the signals transmitted via the uplink dedicated physical control channel (DPCCH) to the serving cell 12. In an instance in which the transmission power for signals transmitted via an uplink channel, such as the uplink DPCCH, is relatively high, the mobile terminal 10 may be located relatively far from the serving cell and/or the mobile terminal 10 may be suffering from uplink interference from other mobile terminals served by the neighbor cells 16. In either instance, a relatively high transmission power for signals transmitted via an uplink channel of the mobile terminal 10 may create interference with the neighbor cells 16.

Additionally or alternatively, the apparatus 20, such as the processor 24, may determine, in one embodiment, the path loss may be determined to be the difference between the value of the primary common pilot channel (CPICH) transmission power as signaled by the network and the CPICH received signal code power (RSCP) as measured by the UE. The path loss of a neighbor cell 16 provides an indication as to the distance between the mobile terminal 10 and the neighbor cell 16. In an instance in which the path loss is relatively small, the mobile terminal 10 may be relatively near the neighbor cell 16, thereby increasing the likelihood that the signal transmissions by the mobile terminal 10 may create interference for the neighbor cell 16. Conversely, in an instance in which the path loss is relatively large, the mobile terminal may be relatively far away from the neighbor cell such that there is a lower likelihood that the signal transmissions from the mobile terminal 10 will create interference for the neighbor cell 16.

The apparatus 20 may additionally or alternatively include means, such as the processing circuitry 22, the processor 24 or the like, for determining other parameters or conditions associated with the operation of the mobile terminal 10 that may be indicative of neighbor cell interference. For example, the apparatus, such as the processor, the communication interface 26 or the like, may receive information provided by the neighbor cell 16, such as via a system information block (SIB), e.g., SIB7, so as to obtain information regarding the uplink interference level of the neighbor cell. Based upon at least some of the foregoing parameters, such as the transmission power, the path loss and/or the uplink interference level, the apparatus 20, such as the processor 24, may determine if the operation of the mobile terminal 10 is creating or is likely to have created interference for the neighbor cells 16.

In one embodiment, the apparatus 20, such as the processor 24, may be configured to compare the transmission power to a first threshold with the transmission power satisfying the first threshold by exceeding the first threshold, to compare the path loss to a second threshold with the path loss satisfying the second threshold by being less than the second threshold and optionally compare one or more other parameters, such as the uplink interference level, to respective thresholds. The thresholds may be pre-defined and stored by memory 28 of the apparatus 20. Alternatively, a network element, such as the serving cell 12, a radio network controller or the like, may notify the mobile terminal of the respective thresholds, such as via an RRC measurement control message or via system information, such as SIB5, SIB11, SIB11bis and/or SIB12.

In an example embodiment and as described herein, the apparatus 20, such as the processor 24, may determine that a reselection condition may be present based on the above described reselection criteria and interference data, alone or in combination. However, the apparatus 20, such as the processor 24, may alternatively or additionally determine that a reselection condition is present based upon the existence of a predetermined amount of data to be transmitted to/from the mobile terminal. For example, when there is only a small amount of data to be transmitted (e.g., a common control channel (CCCH) transmission) then there is a lower probability of a reselection condition and thus a lower chance that a network resource, such as the E-DCH, needs to be suspended. However when there is a larger amount of data, for example an amount of data that exceeds an uplink buffer and/or another predetermined limit, then it is more likely that a reselection condition will occur and a network resource, such as the E-DCH, needs to be suspended. The network resource, such as the E-DCH, may be released and or suspended in order to permit reselection to occur prior to the transfer of the large amount of data.

As shown in operation 34 of FIG. 3, the apparatus 20 may also include means, such as the processing circuitry 22, the processor 24, communications interface 26 or the like, for causing a report to be transmitted. In an embodiment, in an instance in which the apparatus determines the presence of a reselection condition, as described with reference to decision operation 32, then the apparatus may advise a serving cell, a network resource, radio network controller and/or the like, that a network resource, such as the E-DCH, has been released.

In one embodiment, the report that is caused to be transmitted by the apparatus 20, such as the mobile terminal 10, may provide a buffer status, such as an empty buffer status regardless of the actual state of the buffer. For example, the apparatus 20, embodied, for example by the mobile terminal 10, may report an empty buffer status (e.g., Total E-DCH Buffer Status (TEBS)=0 bytes) in the scheduling information (SI) even though the buffer is not empty. Upon receipt of the empty buffer status, the network, such as the serving cell 12, may release the network resource, such as the E-DCH. Once the mobile terminal 10 recovers (e.g. there is no longer interference with a neighbor cell) then the resource, such as the E-DCH, may be resumed or allocated again.

In another embodiment, the apparatus 20, such as the mobile terminal 10, may add a new field to the SI that functions to transmit a report to a network resource, radio network controller and/or the like indicating that the network resource, such as the E-DCH, may need to be suspended. Alternatively or additionally, the new field may also take the form of a special value of TEBS. Alternatively or additionally, the new field may also take the form of a special value of Channel Quality Indication (CQI).

As shown in operation 36 of FIG. 3, the apparatus 20 may also include means, such as the processing circuitry 22, the processor 24, communications interface 26 or the like, for causing a network resource, such as the E-DCH, to be modified in an instance in which the presence of a reselection condition has been identified and a report has provided to the network. In one embodiment, the apparatus 20, such the mobile terminal 10, autonomously releases or suspends the network resource, such as the E-DCH. By autonomously acting, the mobile terminal 10 may reduce latency. In other embodiments, the network resource, such as the E-DCH, may be released while the apparatus 20, such as the mobile terminal 10, is in the CELL-FACH state using an inactive absolute grant. Alternatively or additionally, the use of an inactive absolute grant and/or an autonomous action by the apparatus 20, such as the mobile terminal 10, may also be accompanied by the establishment of a timeout procedure, such as defined by a timer. The timeout procedure defined by the timer may be configured to prevent the requesting of another resource within the timeout procedure or may prevent the mobile terminal from requesting a new resource until the interference conditions are no longer present.

Alternatively or additionally, the apparatus 20, embodied, for example, by the mobile terminal 10, may receive a message using means such as the processor 24 and the communications interface 26, for receiving a message from a serving cell 12, a network resource, radio network controller and/or the like that causes the modification of the network resource, such as the E-DCH as is described with respect to Operation 36 of FIG. 3. In an embodiment, a command (e.g., absolute grant value, high speed shared control channel order, and/or MAC header information) may be received that instructs the mobile terminal to suspend or release the network resource, such as the E-DCH. In another embodiment, the mobile terminal 10 may receive an indication of a modified serving grant (e.g., mobile terminal transmit power is reduced to avoid interference) which causes the mobile terminal 10 to suspend or release the resource.

Alternatively or additionally, a message may indicate that the apparatus 20, embodied by, for example, the processor 24, may apply a specific bias, offset and/or priority to a neighbor cell or frequency when evaluating reselection as shown with respect to Operation 38. For example, applying a specific bias, offset and/or priority to a neighbor cell effectively allows for a fast trigger for cell reselection. In this example, the use of RRC signaling to release the RRC connection and perform redirection may be avoided. The mobile terminal 10 may reselect and maintain the RRC signaling and any packet data protocol (PDP) context to be re-established on the other frequency.

Alternatively or additionally, an apparatus, embodied, by for example, the serving cell 12 may trigger a reselection condition. In some cases the serving cell 12 may trigger a reselection condition without the mobile terminal 12 reporting an interference condition and/or the presence of reselection criteria. A serving cell 12, in an instance in which the network experiences high load on a frequency, may for example, cause a network transmission that indicates a reselection condition as described with reference to FIG. 3 to cause the mobile terminal 10 to modify a network resource, such as the E-DCH for purposes of load balancing. In this example case, the release of the network resource, such as the E-DCH would be triggered by the serving cell 12 (e.g. via High Speed Shared Control Channel order, or inactive grant, etc) and the network command would likely be accompanied by a reselection offset. The reselection offset is configured to cause the mobile terminal 10 to switch to another frequency.

Alternatively or additionally, the apparatus 20, embodied by, for example, by the processor 24, may receive a specific adjustment to for a reselection calculation. For example, a reselection calculation may include applying a temporary bias (such as offset and/or priority) for neighboring cells 16.

As shown in operation 38 of FIG. 3, the apparatus 20 may also include means, such as the processing circuitry 22, the processor 24, communications interface 26 or the like, for causing the reselection of a serving cell. As described herein, the apparatus 20, such as the mobile terminal 10 may perform reselection of a new serving cell to avoid interference situations. Alternatively or additionally, the reselection may include activating a previous serving cell that was suspended or released, by the mobile terminal 10. Alternatively or additionally, in one embodiment, when the reselection criteria are met, the radio resource control (RRC) layer may indicate to the medium access control (MAC) that a network resource, such as an E-DCH resource, should be suspended or released. The suspension or modification of a network resource is further described with reference to operation 34.

As indicated above, the method, apparatus and computer program product of one embodiment are configured to permit a mobile terminal 10 operating in a CELL_FACH to determine the potential for neighbor cell interference and to suspend and/or release a network resource, such as the E-DCH, to trigger reselection of a cell even while the mobile terminal is in the CELL_FACH state. In order to provide further explanation of this embodiment, reference is made to FIG. 4 in which the mobile terminal is initially operating in a CELL_FACH state as shown in operation 40. The apparatus 20 of this embodiment may include means, such as the processing circuitry 22, the processor 24 or the like, for determining whether neighbor cell interference is being caused by the mobile terminal while the mobile terminal is in the CELL_FACH state. See, for example, operation 42 of FIG. 4. As described above, the apparatus, such as a processor, may determine whether neighbor cell interference is being caused by determining whether one or more parameters satisfy respective thresholds and/or whether a reselection criteria is present. For example, to determine the presence of an interference the apparatus, such as a processor, may determine whether the transmission power for signals transmitted via an uplink channel satisfies a respective threshold, whether a path loss for signals received from the neighbor cell satisfies a respective threshold and/or whether an uplink interference level at the neighbor cell satisfies a respective threshold.

In an instance in which the apparatus 20, such as the processor 24, does not determine that neighbor cell interference is being created, the apparatus need not issue suspend and/or release the network resource and, instead, the mobile terminal 10 may continue to operate in the CELL_FACH state while the apparatus continues to monitor the various parameters for an indication of neighbor cell interference and/or the reselection criteria. However, the apparatus may also include means, such as the processing circuitry 22, the processor 24, the communication interface 26 or the like, for causing a measurement report to be provided to a network element, such as the serving cell 12, a radio network controller or other network element, in an instance in which it is determined that neighbor cell interference is being caused. Based on the determined interference with the neighbor cell, in one embodiment, the apparatus may include means, such as the processing circuitry, the processor, the communication interface or the like, for causing a network resource, such as an E-DCH, to be modified. See operation 44 of FIG. 4. As described with respect to operation 36 of FIG. 3, the apparatus may release and/or suspend the E-DCH resource. As shown in operation 46 of FIG. 4, the apparatus 20 may also include means, such as the processing circuitry 22, the processor 24, communications interface 26 or the like, for causing the reselection of a serving cell.

Advantageously, the apparatus 20, method and computer program product as described herein enables a mobile terminal 10 to perform cell reselection when a network resource, such as an E-DCH, is allocated. The apparatus, method and computer program product as described herein further allows flexible conditions as to the suitable conditions to perform reselection (e.g., large amount of data may cause high interference thereby indicating reselection). In some embodiments, the apparatus, method and computer program product as described herein avoids causing interference to neighbor cells 16, radio link failures and dropped calls, while avoiding complex interference control algorithms. The apparatus, method and computer program product as described herein further provides for dynamic load balancing between frequencies with reduced latency and reduced power consumption.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
   determining, using a processor, a presence of a reselection condition based on reselection data, wherein at least a portion of the reselection data comprises an interference indication of an interference level with one or more neighbor cells;
   in an instance in which the presence of the reselection condition is determined, and in an instance in which a data amount to be transmitted exceeds a predetermined limit, causing a network resource to be modified, wherein at least a portion of the predetermined limit is defined by a network element via one or more system information bits;
   causing a report to be transmitted, wherein the report indicates the presence of the reselection conditioning; and
   causing a reselection of a serving cell;
   wherein causing the network resource to be modified further comprises at least one of suspending or releasing, using the processor, the network resource, and the processor being operable to suspend the network resource based on a timeout procedure and release the network resource, and wherein the network resource comprises an enhanced dedicated channel (E-DCH).

2. The method of claim 1 wherein determining the presence of the reselection condition further comprises:
   determining in an instance in which a cell reselection criteria is met;
   determining in an instance in which an interference condition is met;
   determining in an instance in which a network command is received; and
   in an instance in which at least one of the cell reselection, the interference condition is met or the network command is received, causing the presence of the reselection condition.

3. The method of claim 1 wherein causing the report to be transmitted further comprises causing an empty buffer message to be transmitted.

4. The method of claim 1 wherein causing the report to be transmitted further comprises generating a new field in a scheduling information report, wherein the new field indicates the modification of the resource.

5. The method of claim 1 wherein causing the network resource to be modified further comprises generating an inactive grant, while in a CELL-FACH (Forward Access Channel) state; and causing the generated inactive grant to be transmitted.

6. The method of claim 1 wherein causing the network resource to be modified further comprises at least one of receiving a suspension message indicating the suspension of the enhanced dedicated channel (E-DCH) resource, receiving an indication that a serving grant has been modified, or receiving a cell reselection message.

7. The method of claim 1 wherein the serving cell is at least one of the current serving cell and another serving cell.

8. An apparatus comprising:
   at least one processor; and
   at least one memory including computer program code, the at least one memory and the computer program code configured to, with the at least one processor, cause the apparatus at least to:
      determine a presence of a reselection condition based on received reselection data, wherein at least a portion of the reselection data comprises an interference indication of an interference level with one or more neighbor cells;
      in an instance in which the presence of the reselection condition is determined and in an instance in which a data amount exceeds a predetermined limit, cause a network resource to be modified, wherein at least a portion of the predetermined limit is defined by a network element via one or more system information bits;
      cause a report to be transmitted, wherein the report indicates the presence of the reselection condition; and
      cause a reselection of a serving cell;
   wherein the at least one memory and the computer program code are further configured to, with the at least one processor, cause the apparatus to at least one of suspend or release the network resource, and wherein the network resource comprises an enhanced dedicated channel (E-DCH) and wherein the processor is operable to suspend and release the network resource.

9. The apparatus according to claim 8 wherein the at least one memory and the computer program code are further configured to, with the at least one processor, cause the apparatus to:
   determine in an instance in which a cell reselection criteria is met;
   determine in an instance in which an interference condition is met;
   determine in an instance in which a network command is received; and
   in an instance in which at least one of the cell reselection, the interference condition is met or the network command is received, cause the presence of the reselection condition.

10. The apparatus according to claim 8 wherein the at least one memory and the computer program code are further configured to, with the at least one processor, cause the apparatus to cause an empty buffer message to be transmitted.

11. The apparatus according to claim 8 wherein the at least one memory and the computer program code are further configured to, with the at least one processor, cause the apparatus to generate a new field in a scheduling information report, wherein the new field indicates the modification of the resource.

12. The apparatus according to claim 8 wherein the at least one memory and the computer program code are further configured to, with the at least one processor, cause the apparatus to generate an inactive grant, while in a CELL-FACH (Forward Access Channel) state; and causing the generated inactive grant to be transmitted.

13. The apparatus according to claim 8 wherein the at least one memory and the computer program code are further configured to, with the at least one processor, cause the apparatus to receive at least one of a suspension message indicating the suspension of the enhanced dedicated channel (E-DCH) resource, and indication that a serving grant has been modified, or a cell reselection message.

14. A method comprising:
- While in a Cell_FACH (Forward Access Channel) state, determining a presence of uplink interference, wherein the uplink interference includes an indication of an interference level with one or more neighbor cells;
- in an instance where the presence of uplink interference is determined and in an instance in which a data amount exceeds a predetermined limit, causing an enhanced dedicated channel (E-DCH) to be modified and wherein at least a portion of the predetermined limit is defined by a network element via one or more system information bits;
- causing a report to be transmitted, wherein the report indicates the presence of the reselection condition; and
- causing a reselection of a serving cell;
- wherein causing the E-DCH to be modified further comprises at least one of receiving a suspension message indicating a suspension of a E-DCH resource, receiving an indication that a serving grant has been modified, or receiving a cell reselection message.

15. The method of claim 14 wherein determining the presence of uplink interference further comprises:
- determining in an instance in which a cell reselection criteria is met;
- determining in an instance in which an interference condition is met; and
- determining in an instance in which a network command is received; and
- in an instance in which at least one of the cell reselection, the interference condition is met or the network command is received, causing the presence of the reselection condition.

* * * * *